United States Patent
Fouvry et al.

(10) Patent No.: US 9,081,922 B2
(45) Date of Patent: Jul. 14, 2015

(54) METHOD OF FABRICATING A MECHANICAL PART, INCLUDING A METHOD OF PREDICTING THE RISKS OF CRACK INITIATION IN THE PART IN A "FRETTING-FATIGUE" SITUATION

(71) Applicant: AIRBUS HELICOPTERS, Marignane, Cedex (FR)

(72) Inventors: Siegfried Fouvry, Ecully (FR); Stephane Heredia, Velaux (FR); Bruno Berthel, Lyons (FR); Eric Greco, Marignane (FR)

(73) Assignee: Airbus Helicopters, Marignane Cedex (FR)

( * ) Notice: Subject to any disclaimer, the term of this patent is extended or adjusted under 35 U.S.C. 154(b) by 230 days.

(21) Appl. No.: 13/915,895

(22) Filed: Jun. 12, 2013

(65) Prior Publication Data
US 2014/0000080 A1  Jan. 2, 2014

(30) Foreign Application Priority Data
Jun. 28, 2012 (FR) ..................... 12 01826

(51) Int. Cl.
| | |
|---|---|
| G01M 5/00 | (2006.01) |
| G06F 17/50 | (2006.01) |
| G01N 3/56 | (2006.01) |
| G01N 3/32 | (2006.01) |
| B21D 53/92 | (2006.01) |
| B64C 1/00 | (2006.01) |
| B64F 5/00 | (2006.01) |

(52) U.S. Cl.
CPC ......... *G06F 17/5018* (2013.01); *G01M 5/0033* (2013.01); *G01N 3/32* (2013.01); *G01N 3/56* (2013.01); *B21D 53/92* (2013.01); *B64C 2001/0081* (2013.01); *B64F 5/0045* (2013.01); *G01N 2203/0062* (2013.01); *G01N 2203/0064* (2013.01); *G01N 2203/0218* (2013.01); *Y10T 29/49771* (2015.01); *Y10T 29/49776* (2015.01); *Y10T 29/49863* (2015.01)

(58) Field of Classification Search
CPC ................... Y10T 29/49771; Y10T 29/49776; Y10T 29/49863; B21D 53/00; B21D 53/92; B64C 2001/0081; G01M 5/0033; G01M 5/0016; B64F 5/0045
See application file for complete search history.

(56) References Cited

U.S. PATENT DOCUMENTS 5,065,630 A * 11/1991 Hadcock et al. ................ 73/802
2003/0074976 A1    4/2003 Ahmad

OTHER PUBLICATIONS

Mohd Tobi et al.; "A study on the interaction between fretting wear and cyclic plasticity for Ti-6A1-4V"; Wear Elsevier Sequoia, Lausanne, CH, vol. 267, No. 1-4, Jun. 15, 2009, pp. 270-282, XP026133268, ISSN: 0043-1648, DOI: 10.1016/J.Wear.2008.12.039 (extracted on May 23, 2009).

(Continued)

*Primary Examiner* — Jermie Cozart
(74) *Attorney, Agent, or Firm* — Brooks Kushman P.C.

(57) ABSTRACT

A method of fabricating a mechanical part of structure that is defined relative to a predictive search of the risks of crack initiation therein by using a method of calculation by finite elements. A coarse mesh (9) is taken into account, and the individual size of the meshes (20) and a critical distance (d) are defined jointly by an operator. The meshes (20) making up the mesh (9) are defined to be of identical mesh size, with the critical distance (d) being defined as the sum of an integer number of depth dimensions of said meshes (20). If the results of the calculation by finite elements diverge, then a calibration weighting function is advantageously applied that takes account of the size of the meshes (20) by taking account of the critical distance (d).

8 Claims, 2 Drawing Sheets

(56) References Cited

OTHER PUBLICATIONS

S. Naboulsi et al: "Fretting fatigue crack initiation behavior using process volume approach and finite element analysis"; Tribology International, vol. 36, No. 2, Feb. 2, 2003, pp. 121-131, XP055062404, ISSN: 0301-679X DOI: 10.1016/S0301-679X(2)00139-1.

Search Report and Written Opinion; Application No. FR 1201826; dated May 14, 2013.

* cited by examiner

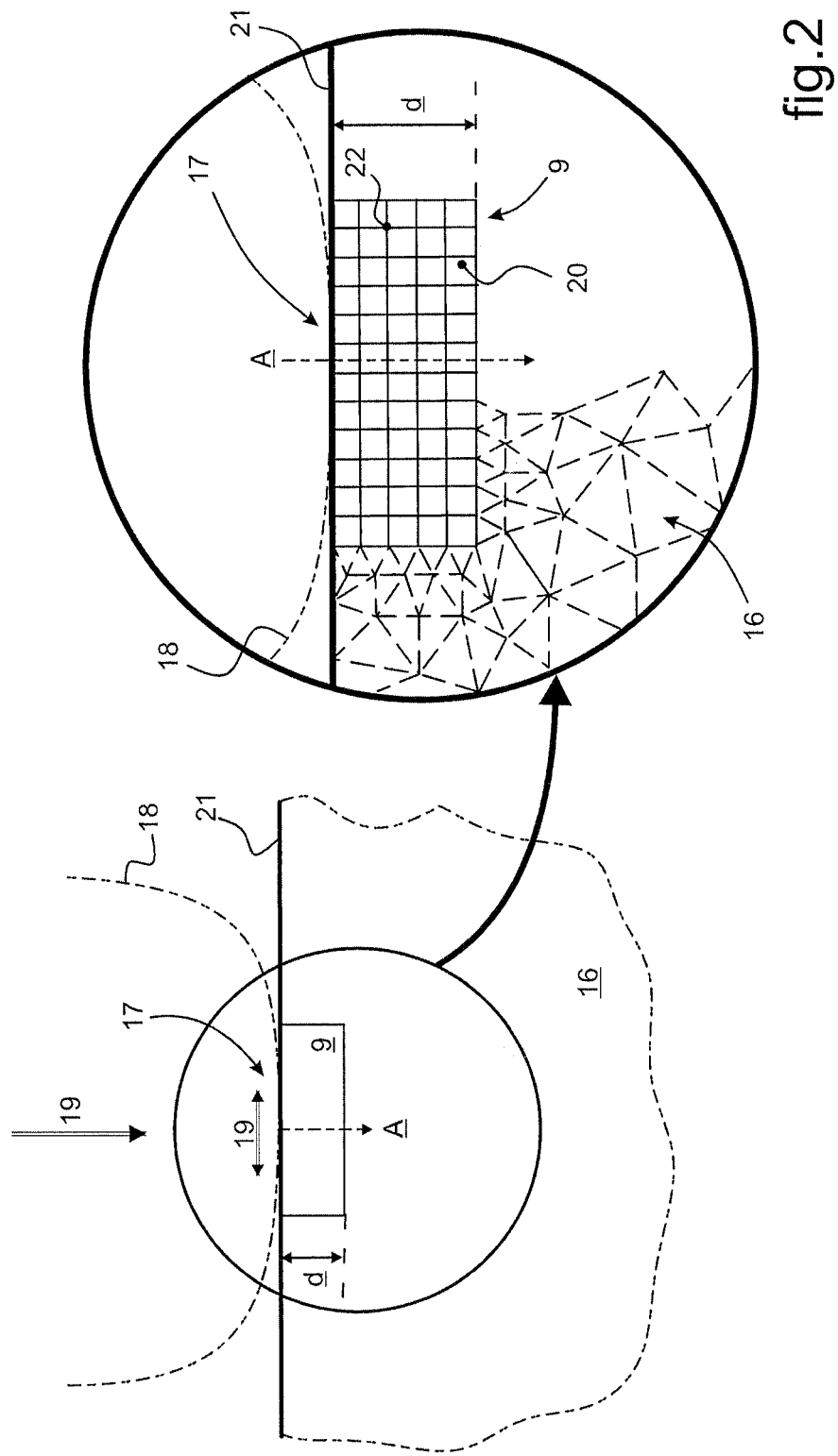

METHOD OF FABRICATING A MECHANICAL PART, INCLUDING A METHOD OF PREDICTING THE RISKS OF CRACK INITIATION IN THE PART IN A "FRETTING-FATIGUE" SITUATION

CROSS REFERENCE TO RELATED APPLICATIONS

This application claims priority to French patent application No. FR 12 01826 filed on Jun. 28, 2012, the disclosure of which is incorporated in its entirety by reference herein.

BACKGROUND OF THE INVENTION (1) Field of the Invention

The present invention relates to the field of research into the mechanical properties of solid materials. The invention relates more particularly to searching for crack initiation conditions in a part that is to be fabricated and that is to be subjected to fretting-fatigue type stresses. Such fretting-fatigue stresses are known to associate microscopic rubbing on a surface with volume deformation such as in twisting, bending, and/or traction-compression situations.

The present invention lies in the context of a method of fabricating a mechanical part, including a method of making a predictive search concerning the risks of crack initiation in said mechanical part in a fretting-fatigue situation. More specifically, said predictive search makes use of a calculation method of the type implementing finite elements.

(2) Description of Related Art

In the context of a method of fabricating a mechanical part, the structure of the mechanical part is determined before the part is made, in particular by taking account of the ability of that mechanical part to withstand the stresses to which it is to be subjected in operation. In this context, a mechanical part may be placed in a fretting-fatigue situation, and it is appropriate to predict the risk of it cracking, given the characteristics of the material from which it is made. For this purpose, calculation methods of the finite element type have been developed that make it possible to predict the risks of crack initiation in a mechanical part made of a given material.

Defining the structure of a part that is to be fabricated by making use of a finite element type calculation method involves a prior operation of performing tests on test pieces in order to evaluate the strength of the material from which the part is to be fabricated. A search is made more specifically to quantify the thresholds from which cracking is initiated in a given material, and then on the basis of information collected during the tests performed, to calibrate a criterion for application of the finite element calculation method in order to predict the risks of crack initiation in the part that is to be fabricated, depending on its dimensions.

In general terms, the method of calculation by finite elements consists in defining a mesh for a stress contact zone on the part that is to be fabricated, and taking account of the stress gradient in the material from which the part is fabricated. The individual meshes have the shape of regular polygons, in particular triangles or squares, and at their vertices they define nodes for which the applied stresses are calculated. For each of the calculated stresses, a risk of crack initiation is deduced by application of a criterion in the form of a coefficient or an equation. In order to take account of the stress gradient in the material, various calculation techniques may be applied, in particular by taking account of a critical distance in depth.

It is conventional to define a fine mesh based on the smallest possible mesh size and on a specific density of meshes over a surface depth of the material. A fine mesh makes it possible to distribute as well as possible and with accuracy the sizes of the meshes defining the separation distances between adjacent nodes, with the applied stresses being calculated for those nodes along predefined paths. From such a fine mesh, it is desired to obtain results that converge, thereby obtaining an estimate of the risks that is as exact as possible, given the application of a method of calculation involving discretization.

More precisely, it is commonly accepted that the finite element calculation method must be convergent, so that error due to discretization can ideally be considered as being zero, providing the fineness and the density of the mesh tend towards a mesh size of zero. Ideally, the size of the meshes should be considered relative to the grain size of the material from which the part is to be fabricated.

In this context, reference may be made to the following documents:

US 2003/0074976 (Ahmad Jalees);

A. L. Mohd Tobi et al. "A study on the interaction between fretting wear and cyclic plasticity for Ti-6A1-AV", Wear, Elsevier Sequoia, Lausanne, CH, Vol. 267, No. 1-4, Jun. 15, 2009 (2009 Jun. 15), pp. 270-282; XP026133268, ISSN: 0043-1648, DOI: 10.1016/J.Wear.2008.12.039 (extracted on 2009 May 23); and S. Naboulsi et al. "Fretting fatigue crack initiation behavior using process volume approach and finite element analysis", Tribology International, Vol. 36, No. 2, Feb. 2, 2003 (2003-02-02), pp. 121-131, XP055062404, ISSN: 0301-679X, DOI: 10.1016/S0301-679X (02)00139-1.

Searching for a result that converges makes it difficult if not impossible to use such a finite element calculation method on an industrial scale for application to predicting the risks of crack initiation in a part that is to be fabricated. Such an ideal method with converging results requires large amounts of calculation time and prevents the computer equipment that is performing those calculations from being used for any other purpose. Such an approach is particularly unsuitable for a material under examination that withstands steep surface stress gradients, such as an alloy based on titanium or a composite material, e.g. a metal-filled ceramic material. As an indication, in order to obtain results that converge, a fine mesh for a material that is subjected to steep surface stress gradients requires meshes of a size that may be as small 5 micrometers (µm), or indeed meshes of a size that is even smaller, especially for a titanium-based alloy.

For example, in the field of aircraft, and more particularly of rotorcraft, the mechanical parts making up a mechanism are subjected in flight not only to fatigue stresses specific to their own operation, but also to fretting stresses generated by the high levels of vibration that such mechanisms need to withstand. The material from which such mechanical parts are made is selected for its characteristics of being lightweight and robust when faced with stresses applied in volume. Nevertheless, the vibration to which mechanical parts are subjected gives rise to micromovements in the zones of contact between them, thereby giving rise to microscopic surface fretting. It should be considered that the shapes of such mechanical parts may well be complex.

In this context, a material that is suitable for fabricating mechanical parts that are subjected to high levels of fretting-fatigue stress on board an aircraft, and in particular a rotorcraft, is a material based on titanium, such as the titanium alloy Ti-10V-2Fe-3Al, or an analogous material that withstands steep stress gradients, which material is selected because of its light weight and its ability to withstand volume stresses.

It has been found that conventional methods of finite element calculation applied to mechanical parts made of a titanium alloy, and in particular for mechanical parts that are complex in shape, are difficult to use on an industrial scale because of the calculation time needed and because of such parts needing to be designed appropriately to avoid them being overdimensioned.

Such difficulties of making use of conventional finite element calculation methods for defining the structure of a part to be fabricated, in particular one made of a titanium alloy, are mentioned in document US 2003/0074976 (Ahmad Jalees).

BRIEF SUMMARY OF THE INVENTION

An object of the present invention is to provide a method of fabricating a mechanical part that might potentially be subjected to fretting-fatigue stresses, by making use of a method of predicting the risks of crack initiation in the parts on the basis of a finite element calculation method that takes account of the surface stress gradient in the material from which the part is fabricated.

The present invention seeks more particularly to propose such a prediction method that can be performed while limiting the calculation operations needed and while avoiding overdimensioning the part that is to be fabricated. Such objects are looked for even when the parts that are to be fabricated are complex in shape and/or made of materials that withstand steep stress gradients, such as titanium-based alloys or composite materials based on ceramics, e.g. with a metal filler.

Said limitation of the calculation operations must nevertheless not degrade the reliability of the prediction that is obtained, and must provide results that are satisfactory, including for parts that are complex in shape and made of a material that withstands steep stress gradients, such that a high level of stress at the surface in such a material decreases rapidly with depth.

The method of the present invention is a method of fabricating a mechanical part, the method comprising an operation of designing said part that is to be fabricated, which operation performs a prediction operation of predicting the risks of crack initiation in the part that is to be fabricated when subjected to fretting-fatigue stresses.

The method of the present invention comprises a test operation performed on test pieces made of a material from which the part that is to be fabricated is to be made. During this test operation at least one test piece is subjected during test cycles to fretting-fatigue stresses in order to quantify the cracking-initiation threshold for a given material.

The test operation makes it possible to determine conditions under which cracking will be initiated in a given material. Such a test operation is performed by an operator using apparatus for applying stresses on at least one test piece. Such apparatus is commonly used in the field of tribology. For each test performed to a given number of cycles, a stress limit that the material can withstand is identified.

In the context of the present invention, it is advantageous to use a stress contact zone, e.g. on a titanium alloy, that is of the type defined by a cylinder and a plane, and to use a number of cycles of applying stress to the test piece that is of the order of $10^6$ cycles. Other configurations for the stress contact zone may be defined, such as the type comprising a sphere and a plane or a plane and a plane.

Still in the context of the present invention and by way of indication, the radius of curvature defining such contact zones having a bearing surface in the form of a surface of revolution is preferably selected to lie in the range 20 millimeters (mm) to 80 mm, approximately. Nevertheless, it is possible to increase or decrease the radius that is selected in order to cover a wider range of stress gradients being generated in the material.

Following the test operation, the method of the present invention then comprises an operation of calculating stresses by a finite element calculation. This calculation operation comprises a prior step of an operator defining a mesh for a contact zone under stress of the part that is to be fabricated, the mesh being appropriate for the tests being performed. After this prior step of defining the mesh, a computer calculation tool is used with operator-determined settings to perform a step of calculating the fretting-fatigue stresses applied to each of the nodes defined by the meshes making up said mesh. In particular, said meshes are individually in the shape of regular polygons.

After the operation of calculating stresses by finite elements, the method of the present invention then comprises a calibration operation by calculation on the previously-calculated stresses. The calculation operation is performed by means of a computer-calculation tool using operator-determined settings, by applying a calculation criterion that is calibrated on the basis of the data provided by the tests previously performed on test pieces.

Said calculation criterion is applied to each of the calculated stresses in order to deduce the risks of crack initiation in the part that is to be fabricated. Said calculation criterion takes account in particular of a critical distance as defined by the operator, said critical distance extending depthwise into the material from the outwardly-facing surface of the material in the contact zone of the part that is to be fabricated.

The calibration operation seeks to correct the previously-performed stress calculations, in particular depending on the calculation code used, the nature of the materials in contact, and the data obtained from the test.

It is specified that said mesh is a surface mesh that extends into the depth of the material from the outwardly-facing face of the material in question facing said contact zone down to a depth in the material that is limited to said critical distance. Said surface mesh may be in the vicinity of a mesh in depth, that is used outside the ambit of the present invention and that may be defined in arbitrary manner, extending around said surface mesh. Such a mesh in depth is for evaluating the stresses applied to the material outside the surface stress fields that are calculated from said surface mesh dedicated to predicting the risks of crack initiation in the part that is to be fabricated.

According to the present invention, such a method of fabricating a mechanical part is mainly recognizable in that the individual size of the meshes and said critical distance are defined jointly in correlation by the operator. The meshes together making up said mesh are defined by individual sizes that are identical, the critical distance being defined by summing an integer number of depth dimensions of said meshes of identical individual size.

The mesh is preferably selected as being a quadrangular mesh with the size of the regular meshes being considered relative to the size of one of their sides. In compliance with the correlation between the selections performed jointly concerning both the critical distance and the size of the meshes, in the context of a mesh that is quadrangular or even square, consideration is given to the sides of the meshes that extend in depth and relative to the critical distance. By analogy, if a triangular mesh is selected, then the size of meshes having a regular triangular shape corresponds to the size of one of the heights of the triangles.

The concept of "depth" should be considered along an axis extending in the depth direction into the depth of the material from the outwardly-facing face in question of the material in the contact zone.

The stress calculation is performed at the nodes of the meshes. After stresses have been calculated, paths are defined for averaging and smoothing said calculations. The paths are virtual lines passing through pluralities of nodes and recording the stresses at each of the intersections between a path and nodes. By way of illustration, in the preferred configuration in which the mesh is made up of meshes of a single size extending in depth from the contact zone towards the node at the depth under consideration given the critical distance, two paths are taken into consideration. One of the paths is created at the surface node of the mesh and the other path is created at the deep node pointed to by the critical distance.

As an indication, it has been found that meshes having an individual size lying in the range 0.05 times the critical distance to the critical distance in full provide a result that is satisfactory.

Selecting meshes that are identical in size makes it possible to enlarge mesh size in order to reduce calculation time, while ignoring the lack of convergence in the results. By selecting a close correlation between the critical distance and the size of one or more identical meshes summed in the depth direction, it is possible for there to be no such search for converging results, without that harming the pertinence of the predicted risk of crack initiation in the part that is to be fabricated. On the basis of such a selection, a weighting function is applied during the calibration operation, said weighting function being a function for correcting diverging results coming from the finite element calculation operation.

If the calculation operation by finite elements diverges, the calibration operation performs a weighting function to correct said divergent nature of the calculation operation. More particularly, when the finite element calculation operation is defined as diverging on the basis of the mesh proposed by the present invention, the calibration operation uses a weighting function for correcting said diverging nature of the calculation operation. The diverging nature of said calculation operation is the result in particular of the advantageous use of a mesh that is coarse and of a number of test cycles that is limited.

The calibration operation advantageously comprises applying a weighting function by means of a coefficient $k(l)$, on the basis of which weighting function said calculation criterion is defined in the context of defining the size of the meshes and the critical distance together. The coefficient $k(l)$ is a weighting coefficient for stress calculations determined on the basis of the results of the test operations, and it serves to take account of the various parameters that are predefined by the finite element calculation. Such parameters relate in particular to the size of the meshes and to the critical distance that is selected in correlation therewith, representing the overall size of the contact zone under consideration during the test operation.

The weighting function is defined more particularly by taking account of the size of the mesh or the sum of the sizes of identical meshes that are juxtaposed depthwise, which sizes have values that depend on the value of the critical distance. The stress that is considered to be maximal in depth at the critical distance is multiplied by the weighting function, which takes account of the stress gradient, and either the mesh size is selected to be equal to the critical distance or the sum of the mesh sizes in the depth direction is selected to be equal to the critical distance when the mesh is selected to have a plurality of juxtaposed meshes in the depth direction.

Said weighting function is such that:

$$\omega = 1 + k(l) \cdot \nabla \sigma_{max}$$

in which:

$\omega$ is said weighting function;

$k(l)$ is a weighting coefficient for weighting the stress calculations and it is determined from results obtained during the test operations; and $\nabla \sigma_{max}$ is the stress gradient in the material.

The weighting function is preferably defined as depending on the maximum stress gradient in the material between the outwardly-facing face of the contact zone and the critical distance considered in correlation with the size of the mesh or the juxtaposed meshes in the depth direction. By analogy, it is possible to envisage analyzing a mean stress gradient, a hydrostatic pressure gradient, or any other stress gradient associated with the applied forces.

The coefficient $k(l)$ is determined more specifically for each of the test configurations, with a mean value for the coefficient $k(l)$ being deduced from said determinations for each of the test configurations for use when calculating said criterion. For each node under consideration in the depth direction, the theoretical value is calculated for the coefficient $k(l)$, and then the coefficients $k(l)$ calculated for each of the nodes are averaged.

From said determinations for each of the test configurations, a mean value is deduced for the coefficients $k(l)$. The coefficient $k(l)$ is determined in particular on the basis of the following rule:

$$\sigma_{max}(z) \cdot (1 + k(l) \cdot \nabla \sigma_{max}) = \sigma_d$$

in which:

$\sigma_{max}(z)$ is the stress calculated at depth of the node of a mesh under consideration at the critical distance $(z)$; by way of example, the calculated stress is a maximum stress, an average stress, or a stress amplitude;

$(1 + k(l) \cdot \nabla \sigma_{max})$ is a weighting function for calibration from said data provided by the test performed during the test operation, in which $\nabla \sigma_{max}$ is the stress gradient in the material, and $k(l)$ is a said correction coefficient of the rule by weighting stress calculations; and $\sigma_d$ is the stress limit that can be withstood by the material. For example, such a stress limit is a fatigue limit of the material, a fretting-fatigue limit of the material, an elasticity limit of the material, or indeed a breaking limit of the material.

Applying the weighting function by means of the correction coefficient $k(l)$ makes it possible to make the pertinence of the looked-for prediction more reliable by mitigating the divergent results of the stress calculation that result from using a coarse mesh. The pertinence of the prediction is made reliable by taking account of said weighting function with reference to a critical distance and to a mesh size that is determined in correlation therewith. The weighting function applied by means of the coefficient $k(l)$ is valid for a definition selected by the operator for any mesh size in correlation with the critical distance, even for a mesh that is coarse, with that having the advantage of limiting calculation time.

As a result of performing the calculation operation, a risk of crack initiation in the part that is to be fabricated can be deduced. Such a risk of crack initiation is determined in particular by applying the following rule:

$$\frac{\sigma_{max}(z) \cdot (1 + k(\ell) \cdot \nabla \sigma_{max})}{\sigma_d} < 1$$

in which:

$\sigma_{max}(z)$ is the stress calculated at the depth of the node of a mesh under consideration at the critical distance;

$(1+k(l)\cdot\nabla\sigma_{max})$ is a weighting function for calibration from said data provided by the tests, in which $\nabla\sigma_{max}$ is the stress gradient in the material and k(l) is a correction coefficient of the rule by weighting stress calculations, k(l) being determined from the results of the test operations; and $\sigma_d$ is the stress limit that can be withstood by the material.

It should be considered that the rule forms the criterion for predicting a risk of crack initiation in the part that is to be fabricated. For the criterion having a value that is less than unity, there is no risk of crack initiation for a given test cycle. Conversely, a criterion that is greater than unity reveals that there is such a risk of crack initiation.

The method of the present invention is advantageously applicable to fabricating a part that is to be fabricated from a titanium alloy. By way of indication for such an application, the individual size of the meshes is preferably defined as lying in the range 50 μm to 200 μm, and the critical distance is defined as lying in the range 50 μm to 600 μm.

A satisfactory compromise between reducing calculation time and obtaining a pertinent outcome from the resulting divergent results after correction by the weighting function, is a critical distance and an individual mesh size selected as a single mesh in depth that is of the order of 100 μm for a titanium alloy such as the Ti-10V-2Fe-3Al alloy. A mesh with meshes of smaller size or conversely of coarser size could nevertheless be applied, with such a mesh being selected by the operator depending on the general rule set out for the present invention in order to obtain best results for said compromise.

In an ideal implementation seeking to limit calculation operations without significantly affecting the pertinence of the deduction that is obtained, the mesh size is equal to the critical distance, and said integer number is equal to 1.

In a preferred implementation, said stress contact zone is of the type defined as a cylinder and a plane with a test piece being subjected to stress cycles amounting to about $10^6$ cycles. The radius of curvature defining said contact zones lies in the range 20 mm to 80 mm, approximately.

Since the structure of the part that is to be fabricated is previously defined by applying said design operation, on the basis of performing the finite element calculation method having the various operations specified above, the method of the present invention includes a final operation of fabricating the part that is to be fabricated.

The solution proposed by the present invention makes it possible to take account of fretting-fatigue stress when dimensioning structures, while limiting the number of calculation operations that need to be performed. The proposed mesh is selected to be coarse with results that are potentially divergent, against the practice in the field. Such a lack of converging results is ignored by applying the calibration operation, which operation takes a weighting function into account that incorporates a coefficient for correcting the stress calculations resulting from the finite element calculation operation, said coefficient incorporating a parameter relating to a critical distance that is defined as being identical to the integer number sum of the dimensions of said meshes of individual sizes that are juxtaposed in the depth direction. Said integer number is potentially equal to unity, without affecting the pertinence of the prediction of crack initiation in the part that is to be fabricated.

The solution proposed by the present invention is applicable industrially at reduced cost by limiting the number of calculation operations, including for parts that are to be fabricated that are complex in shape and that are made of a material that withstands steep stress gradients. Furthermore, the solution proposed by the invention in question makes it possible to avoid overdimensioning the part that is to be fabricated as a result of a pertinent formulation for said calculation criterion, in spite of selecting a mesh that is coarse.

BRIEF DESCRIPTION OF THE SEVERAL VIEWS OF THE DRAWINGS

An implementation of the present invention is described with reference to the figures of the accompanying sheets, in which:

FIG. 2 shows an example of the mesh used by a finite element calculation method in order to predict the initiation of cracking in the mechanical part that is to be fabricated by performing the method shown diagrammatically in FIG. 1.

DETAILED DESCRIPTION OF THE INVENTION

Figure 1:
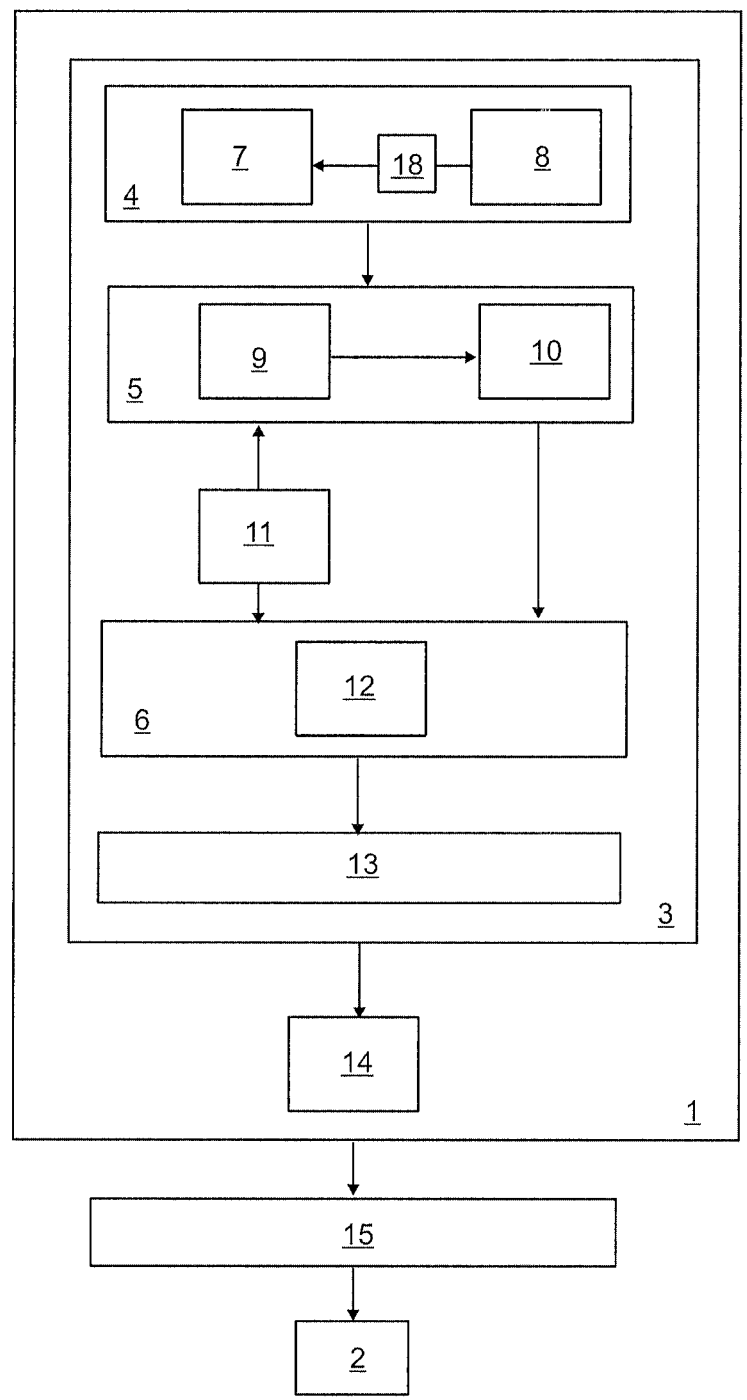
FIG. 1 is a diagram showing the various operations performed by a method in accordance with the present invention in order to fabricate a mechanical part that might potentially be subjected in operation to fretting-fatigue stresses.

In FIG. 1, a method of fabricating a mechanical part includes an operation 1 of designing the part 2 that is to be fabricated. The design operation 1 serves to define the structure of the part 2 that is to be fabricated, by taking account of the stresses to which the part 2 that is to be fabricated will be subjected when in operation. The design operation 1 seeks to specify shapes and dimensions for the part 2 that is to be fabricated in compliance with a given material selected for making it. It should be considered that the fabrication method may implement other operations that do not form part of the techniques that are used in the context of the present invention and that are specifically dedicated to predicting the risks of cracking beginning in the part 2 that is to be fabricated.

The design operation 1 includes a predictive search 3 for the initiation of cracking in the part 2 that is to be fabricated, the search essentially involving a test operation 4 performed on test pieces, a calculation operation 5 for calculating stresses by finite elements, and a calibration operation 6 of calibrating the previously-calculated stresses.

The test operation 4 is performed on test pieces 7 made of the material selected for making the part 2 that is to be fabricated, and it is performed by means of tribological apparatus 8 that is known in the field of research into the mechanical properties of solid materials. By way of example, the test pieces 7 are in the shape of plates or the like, and they are subjected to fretting-fatigue stresses by means of a peg 18 having a cylindrical or spherical bearing surface. The test operation 4 serves to quantify the threshold at which cracking is initiated in the selected material.

The calculation operation 5 is based on a method of calculation by finite elements. A prior step of defining a mesh 9 in a contact zone under stress in the part that is to be fabricated is performed by an operator. From the mesh 9, a stress calculation step 10 is performed by a computer tool 11 using operator-determined settings. Fretting-fatigue stress calculations applied to each of the nodes of the mesh 9 are performed following predefined paths.

The calibration operation 6 serves to correct the previously-calculated stresses over a depth of material that is defined by a critical distance. The calibration operation 6 is performed by the computer tool 11 using operator-determined settings, on the basis of applying a calculation criterion 12 calibrated from the results of the test operation 4. The calculation criterion 12 is applied to each of the calculated stresses in order to deduce the risks of crack initiation in the part 2 that is to be fabricated.

The calibration criterion 12 takes account of a weighting function for correcting divergent results that come from the calculation operation 5. Such divergent results are the result of using a coarse mesh 9, which makes it possible to reduce the number and the duration of stress calculations that need to be performed. In order to perform such a weighting function, it is decided from the step of defining the mesh 9 to give consideration firstly to meshes of identical individual size from one mesh to another, and secondly to a critical distance that is selected in correlation with the mesh 5. On the basis of this selection, the calculation criterion 12 is defined by taking account of a critical distance that corresponds to the individual size of the meshes, and divergent results can be corrected so as to lead to a reliable prediction of the risks of crack initiation the part 2 that is to be fabricated.

At the end of applying the predictive search method 3, and in particular of applying the calibration operation 6 to the results of the calculation operation 5, the looked-for prediction 13 is obtained of the risks of crack initiation in the part 2 that is to be fabricated.

Once the structure of the part 2 that is to be fabricated has been defined, the method performs a verification operation 14 by testing the deductions obtained by calculation on a prototype. Once the operation 1 of designing the part 2 that is to be fabricated has been finished, the part 2 is fabricated in a final fabrication step 15.

In FIG. 2, a said mesh 9 is defined to predict the risks of crack initiation in a part that is to be fabricated in compliance with the provisions of the present invention. Consideration is given to a surface mesh 9 that is used for obtaining such a prediction, with it being possible for any depth mesh 16 to be used for the vicinity of the surface mesh 9. In the implementation shown, said mesh 9 that is taken into consideration for the contact zone 17 is preferably a quadrangular mesh. Such a mesh could also be a square mesh or a triangular mesh.

By way of example, tests are performed on test pieces that are plane, while using a peg 18 that is spherical or cylindrical in shape. The contact zone 17 is defined in particular relative to the characteristics of the peg 18 via which fretting-fatigue stresses 19 are applied to the test pieces.

The mesh 9 extends in depth over a critical distance d with some number of meshes 20 that are of identical individual size, as defined by the operator in correlation with the definition of the critical distance d. More particularly, the critical distance d is defined by summing an integer number of individual dimensions in the depth direction of said meshes 20 that are of identical individual size. Since the meshes 20 are regular in shape, said integer number corresponds to the number of meshes 20 that are juxtaposed depthwise in the material down to the limit defined by the critical distance d. Such an extension of the mesh 9 in the depth direction is to be taken into consideration along a depth axis A that extends from the face 21 of the contact zone 17 facing towards the outside of the material.

In the implementation shown, said integer number of meshes 20 that are juxtaposed in the depth direction is five. The critical distance d may have a dimension of 500 μm, for meshes 20 with an individual size of 100 μm. The individual size of the meshes 20 corresponds to the dimension of one of their sides for a quadrangular mesh as shown, or indeed for a square mesh, or by analogy to the height of a mesh that is in the shape of a regular triangle for a triangular mesh. Between them, the meshes 20 define nodes 22 of the mesh 9, with operations of calculating applied stresses being performed for each of said nodes 22 along predetermined paths.

What is claimed is:

1. A method of fabricating a mechanical part, the method comprising an operation of designing said part that is to be fabricated, which operation performs a prediction operation of predicting the risk of crack initiation in the part that is to be fabricated when subjected to fretting-fatigue stresses, said method comprising:
   a test operation performed on test pieces made of a material from which the part that is to be fabricated is to be made, during which test operation at least one test piece is subjected during test cycles to fretting-fatigue stresses in order to quantify the cracking-initiation threshold for a given material;
   a calculation operation of calculating stresses by finite elements, the operation including a prior step of an operator defining a mesh for a contact zone under stress of the part that is to be fabricated and given the tests that are performed, followed by a step of calculating the fretting-fatigue stresses applied to each of the nodes defined by the meshes making up said mesh and individually having the shape of regular polygons;
   a calibration operation of calibration by calculation on the previously-calculated stresses, by applying a calculation criterion calibrated from the data provided by the testing previously performed on test pieces, said calculation criterion being applied to each of the calculated stresses in order to deduce the risks of crack initiation in the part that is to be fabricated, said calculation criterion taking account of a critical distance (d) defined by the operator and extending depthwise into the material from the surface facing towards the outside of the material in said contact zone of the part that is to be fabricated; and then
   a final fabrication operation of fabricating the part that is to be fabricated with structure as previously defined by applying said design operation;
the method being characterized:
   in that the individual size of the meshes and said critical distance (d) are defined jointly in correlation by the operator, the meshes together making up said mesh being defined by individual sizes that are identical, the critical distance (d) being defined by summing an integer number of depth dimensions of said meshes of identical individual size; and
   if the calculation operation by finite elements diverges, the calibration operation performs a weighting function to correct said divergent nature of the calculation operation.

2. A method according to claim 1, wherein the individual size of the meshes lies in the range 0.05 times the critical distance (d) to the critical distance (d) in full.

3. A method according to claim 1, wherein the calibration operation comprises applying a weighting function based on a coefficient k(l) from which said calculation criterion is defined, said weighting function being such that:

$$\omega = 1 + k(l) \cdot \nabla \sigma_{max}$$

in which:
- ω is said weighting function;
- k(l) is a weighting coefficient for weighting the stress calculations and it is determined from results obtained during the test operations; and
- $\nabla\sigma_{max}$ is the stress gradient in the material.

4. A method according to claim 3, wherein the coefficient k(l) is determined for each of the test configurations, and from said determinations for each of the test configurations, a mean value is deduced for the coefficients k(l), the coefficient k(l) being determined using the following rule:

$$\sigma_{max}(z)\cdot(1+k(l)\cdot\nabla\sigma_{max})=\sigma_d$$

in which:
- $\sigma_{max}(z)$ is the stress calculated at depth of the node of a mesh under consideration at the critical distance (z);
- $(1+k(l)\cdot\nabla\sigma_{max})$ is a weighting function for calibration from said data provided by the test, in which $\nabla\sigma_{max}$ is the stress gradient in the material and k(l) is a said correction coefficient of the rule by weighting stress calculations; and
- $\sigma_d$ is the stress limit that can be withstood by the material.

5. A method according to claim 1, wherein a risk of crack initiation in the part that is to be fabricated is determined by applying the following rule:

$$\frac{\sigma_{max}(z)\cdot(1+k(\ell)\cdot\nabla\sigma_{max})}{\sigma_d}<1$$

in which:
- $\sigma_{max}(z)$ is the stress calculated at the depth of the node of a mesh under consideration at the critical distance (z);
- $(1+k(l)\cdot\nabla\sigma_{max})$ is a weighting function for calibration from said data provided by the tests, in which $\nabla\sigma_{max}$ is the stress gradient in the material and k(l) is a correction coefficient of the rule by weighting stress calculations, k(l) being determined from the results of the test operations; and
- $\sigma_d$ is the stress limit that can be withstood by the material.

6. A method according to claim 1, wherein the method is applied to a part that is to be fabricated from a titanium alloy, and the individual size of the meshes is defined to lie in the range 50 μm to 200 μm, and the critical distance (d) is defined to lie in the range 50 μm to 600 μm.

7. A method according to claim 1, wherein the size of a mesh is equal to the critical distance (d), said integer number being equal to 1.

8. A method according to claim 1, wherein said contact zone is of the type defined as a cylinder and plane with a test piece being subjected to stress cycles amounting to about $10^6$ cycles, and with a radius of curvature defining said contact zones lying in the range 20 mm to 80 mm, approximately.

* * * * *